United States Patent [19]

McGilvery

[11] 4,115,307

[45] Sep. 19, 1978

[54] PHOSPHATE COMPOSITION

[75] Inventor: James D. McGilvery, Etobicoke, Canada

[73] Assignee: Erco Industries Limited, Islington, Canada

[21] Appl. No.: 806,197

[22] Filed: Jun. 13, 1977

Related U.S. Application Data

[63] Continuation-in-part of Ser. No. 640,741, Dec. 15, 1975, abandoned.

[30] Foreign Application Priority Data

Dec. 13, 1974 [GB] United Kingdom ............... 53900/74

[51] Int. Cl.$^2$ .......................... A61K 7/50; C02B 5/04; C11D 7/14; C11D 11/00
[52] U.S. Cl. ................. 252/135; 23/313 R; 252/139; 252/175; 252/184; 252/188.3 R; 424/44; 424/128
[58] Field of Search ............. 23/313; 252/99, 109, 252/135, 139, 175, 184, 188.3; 424/44, 128

[56] References Cited

U.S. PATENT DOCUMENTS

| | | | |
|---|---|---|---|
| 2,414,969 | 1/1947 | Moose | 252/175 |
| 2,494,828 | 1/1950 | Munter | 252/175 |
| 2,515,880 | 7/1950 | MacMahon | 252/135 |
| 3,189,433 | 6/1965 | Hollingsworth | 23/313 X |
| 3,425,948 | 2/1969 | Otrhalek | 252/558 |
| 3,620,972 | 11/1971 | Fite | 23/313 X |
| 3,630,930 | 12/1971 | Davis | 252/531 |
| 3,701,737 | 10/1972 | Goldstein | 23/313 X |
| 3,723,327 | 3/1973 | van Kampen | 252/110 |

*Primary Examiner*—Dennis L. Albrecht
*Attorney, Agent, or Firm*—Sim & McBurney

[57] ABSTRACT

A low density, free-flowing, granular phosphate product having a high oil absorption capacity and capable of dissolving in water to provide a solution of pH about 7 to 8 is provided by mixing a hydratable alkali metal phosphate, polyphosphoric acid, and sodium carbonate and/or sodium bicarbonate and granulating the mixture with water.

13 Claims, No Drawings

PHOSPHATE COMPOSITION

REFERENCE TO RELATED APPLICATION

This application is a continuation-in-part of my co-pending application Ser. No. 640,741 filed Dec. 15, 1975 (now abandoned).

FIELD OF INVENTION

The present invention relates to a novel phosphate composition for use in sequestrant applications.

BACKGROUND TO THE INVENTION

The sequestering properties of phosphates are well-known and are widely employed in a variety of uses, such as the formulation of detergents. Certain cosmetic and other preparations require a good sequestrant in a form which will absorb considerable quantities of organic liquids, such as, bath oil preparations.

Low density granular phosphate-based products have been used in preparations of this type, but generally when they are dissolved in water, they produce a solution having an alkaline pH, which may be undesirable in certain circumstances.

SUMMARY OF INVENTION

In accordance with the present invention, there is provided a low density, free-flowing, granular phosphate product having a high oil absorption capacity and capable of dissolving in water to provide a solution of pH about 7 to 8. The present invention also provides methods for the preparation of such products.

The products of the invention are prepared from a hydratable alkali metal phosphate, a polyphosphoric acid, sodium carbonate and/or sodium bicarbonate and water. The products have a low density, generally in the range of about 0.5 to about 0.8 g/cc and preferably about 0.55 to about 0.65 g/cc.

The oil adsorption capacity of the product of the invention is high, generally about 50% to about 80%, preferably about 65 to about 75%. In the present application, the value of the "oil adsorption capacity" is determined by adding increasing amounts of mineral oil to a fixed amount of the product and determining the point at which the product becomes saturated with oil. The weight of oil which can be absorbed by a unit weight of product, expressed as a percentage, is the oil adsorption capacity of that product.

The present invention provides a low density high oil absorbant granular phosphate from low cost polyphosphates in the form of polyphosphoric acid.

The quantities of the components of the composition may be varied and interrelated over a wide range of values as discussed below consistent with the desire to provide a low density, oil absorbant, dry, free-flowing, granular product which will produce an aqueous solution of neutral or near neutral pH on dissolving in water.

The granules are formed from:
about 45 to about 85% by weight of the alkali metal phosphate,
about 9 to about 30% by weight of the polyphosphoric acid,
about 1.5 to about 23% be weight of the sodium carbonate and/or sodium bicarbonate, and
about 4 to about 17% by weight of water.

GENERAL DESCRIPTION OF INVENTION

The present invention will be discribed more particularly with reference to sodium tripolyphosphate (STPP) as the hydratable alkali metal phosphate. However, the present invention is not limited thereto, but is applicable to a wide variety of other alkali metal phosphates which are neutral or alkaline, including tetrasodium pyrophosphate (TSPP), tetrapotassium pyrophosphate (TKPP), potassium tripolyphosphate (KTPP), trisodium phosphate (TSP), disodium phosphate (DSP), tripotassium phosphate (TKP) and dipotassium phosphate (DKP).

The quantity of alkali metal phosphate used is generally in the range of about 45 to about 85% by weight, preferably about 46.5 to about 75.5% by weight and particularly about 65 to about 75.5% by weight.

The polyphosphoric acid used in the present invention acts as a binding agent in the granulation of the composition and is relatively inert towards the alkalis present until water is added. It is necessary, therefore, to provide a $P_2O_5$ content of at least 75% otherwise reaction with the alkalis can occur. The inertness of the polyphosphoric acid towards the alkalis increases with $P_2O_5$ content and hence higher acid concentrations are preferred. A practical upper limit of $P_2O_5$ concentration is about 85% owing to the lack of commercial availability of such materials and the very high viscosity of such materials which renders distribution of the material in the alkali components difficult. It is preferred, therefore, to utilize a polyphosphoric acid concentration of about 81 to 82% $P_2O_5$.

The quantity of polyphosphoric acid utilized relative to the other components may vary widely, depending on a number of factors, including the necessity to maintain a dry solid composition, the water absorbency capacity of the other components, the desired degree of effervescence of the final product and the degree of expansion required.

Generally, the quantity of polyphosphoric acid is about 9 to about 30% by weight and should be sufficient to react with all the alkali present in the composition upon formation of an aqueous solution of the composition in water.

The quantity of sodium carbonate and/or sodium bicarbonate used in the preparation of the formulation, generally is from about 1.5 up to about 23%. It is usually preferred, however, to utilize less than the maximum, due to difficulties in controlling effervescence at high $Na_2CO_3$ concentrations. Preferably, the sodium carbonate is present in an amount of about 2 to about 10% of the total weight of the composition. It usually is preferred to utilize quantities towards the high end of this range, together with an equivalent quantity of polyacid, so that after granulation, as described in more detail below, high residual quantities of unreacted polyacid and sodium carbonate remain, so that satisfactory effervescence and a fast rate of dissolution may be provided in use.

While sodium bicarbonate may be used in place of the sodium carbonate, it is usually less preferred to do so due to the relative costs of these materials. The invention will be described hereinafter more particularly with reference to sodium carbonate.

A particular granular product is formed from:
about 65 to about 75.5% by weight of the alkali metal phosphate,
about 9.2 to about 30% by weight of the polyphosphoric acid, about 1.8 to about 23% by weight of the sodium carbonate and/or sodium bicarbonate, and
about 4 to about 15% by weight of water.

Typical products formulated in accordance with the procedures of the present invention are formed from the following components:

65 to 75%: STPP
11 to 13%: Polyphosphoric acid (81 to 82% $P_2O_5$)
2 to 10%: $Na_2CO_3$
12 to 13%: $H_2O$ The product of the invention may be formed by a variety of procedures. In the first step of one such procedures, a dry, free-flowing mixture of STPP, polyphosphoric acid and sodium carbonate and/or sodium bicarbonate is prepared. This mixture is formulated so that if dissolved in water, a pH of about 7 to 8 is obtained.

The free-flowing mixture may be prepared by mixing directly together the required quantities of STPP, polyphospric acid and sodium carbonate in a single step. Alternatively, the STPP may be blended with a small amount of sodium carbonate, followed by mixing with polyphosphoric acid in an amount sufficient to provide a mixture which would have a pH of 4.0 to 4.5 if dissolved in water. The resulting mixture is dry and free-flowing. The required amount of sodium carbonate then is added to this mixture to provide the final neutral mixture.

Additionally, an initial mixture of STPP and polyphosphoric acid may be formed containing a higher acid/STPP ratio than is required in the final product. The remainder of the STPP together with the required sodium carbonate then are dry blended with the initial mixture. This procedure in some cases leads to the provision of a more free-flowing product.

The mixture of STPP, polyphosphoric acid, and sodium carbonate formed in this first step is a dry, free-flowing powder showing no evidence of the evolution of carbon dioxide.

In the second step of the process, the latter mixture is granulated by addition of a small amount of water, generally from about 4 to about 17% by weight of the mixture. The addition of the water in the granulation step usually is carried out by the use of a very fine mist, since the latter leads to a narrow range of granule sizes in the granular product.

The addition of this water, which dilutes the polyphosphoric acid, thereby increasing its acidity, results in the evolution of carbon dioxide in the mixture in the plastic state to provide a dry and free-flowing granular powder of very porous low density phosphate particles having high oil absorption properties.

An alternative method for forming the granulated product involves the initial formation of a dry, free-flowing mixture of the STPP and polyphosphoric acid. This may be achieved by directly mixing the required quantities of STPP and polyphosphoric acid or by mixing part of the STPP and polyphosphoric acid and then blending the remainder of the STPP with the mixture.

An aqueous sodium carbonate or sodium bicarbonate solution containing the required quantities of sodium carbonate or sodium bicarbonate then is sprayed onto the STPP/polyphosphoric acid mixture to provide the desired granular product.

Following or during the addition of the water, a tumbling period may be required to obtain a dry granule. Additional quantities of water may be added following tumbling, if desired, to achieve additional granulation and swelling.

The product contains residual quantities of unreacted sodium carbonate and polyphosphoric acid which result in effervescence of the water into which the product is placed.

EXAMPLES

EXAMPLE 1

A dry, free-flowing mixture of 83 parts of STPP, 15 parts of polyphosphoric acid (81.9% $P_2O_5$) and 2% sodium carbonate was prepared. The mixture was granulated by the addition of about 10% water in a Patterson-Kelley Twinshell Liquid/solid (P.K.) blender. A dry, free-flowing neutral granular product was obtained which was analyzed and had properties as follows:

$P_2O_5$ (Total): 56.5%
$P_2O_5$ (Ortho): 3.1%
$H_2O$ at 150° C: 3.4%
pH (1% solution): 7.1
Bulk density: 0.59 gm/cc
$-10/+100$ mesh: 99%
$-10/+40$ mesh: 85%
Oil Absorbency: 75%

EXAMPLE 2

In a P.K. blender STPP was blended with 1.3% of sodium bicarbonate and polyphosphoric acid (81% $P_2O_5$) was added to provide a mixture having a pH of 4.0 to 4.5 when dissolved in water. Sodium carbonate then was added to provide a neutral mixture in which there was no evidence of $CO_2$ production. The resulting mixture was analyzed:

STPP Powder: 51.2%
Polyphosphoric acid: 24.8%
$NaHCO_3$: 1.3%
$Na_2CO_3$: 22.7%

10 parts by weight of water then were added to granulate the mixture and the evolution of $CO_2$ was observed, resulting in a low density, very porous, dry and free-flowing product.

Upon dissolving in water to give a 1% solution, effervescence was observed and the solution had a pH of 6.9.

EXAMPLE 3

A dry free-flowing mixture of 50.0 parts of STPP, 14.4 parts of polyphosphoric acid (81.9% $P_2O_5$) and 11.2 parts of sodium carbonate was prepared in a P.K. blender. The mixture, if dissolved in water, would have had a pH less than 7. An additional 24.4 parts of STPP was then added to provide a dry free-flowing neutral mixture in which there was no evidence of carbon dioxide production. The mixture was granulated by the addition of about 12% water in a rotary drum granulator. A dry free-flowing neutral granular product was obtained which was analyzed and had properties as follows:

$P_2O_5$ (Total): 51.2%
$P_2O_5$ (Ortho): 11.2%
$Na_2CO_3$: 8.5%
$H_2O$ at 105° C: 6.8%
pH (1% solution): 7.7
Bulk density: 0.54 g/cc
$CO_2$ evolution on dissolution: 115 ml/10 g
$-10/+100$ mesh: 92.3%
$-10/+40$ mesh: 78.8%

Oil Absorbency: 80%

EXAMPLE 4

To a P.K. blender were charged 50.0 parts of STPP. 6.25 parts of 82% $P_2O_5$ polyphosphoric acid were added at a temperature of about 80 to 90% through a dispersion bar followed by 1.25 parts of sodium carbonate. The mixture was dry blended for 5 to 10 minutes before being discharged to a tempering drum.

In a finely atomised form 8.45 parts of water was added while the tempering drum was rotated for about 20 minutes.

The product obtained analyzed as follows:

| | |
|---|---|
| Total $P_2O_5$ | 54.5% |
| %$P_2O_5$ present as ortho | 10.7 |
| pyro | 33.5 |
| tri | 53.0 |
| hipoly | 2.8 |
| % $Na_2CO_3$ | 2.4 |
| % $H_2O$ at 105° C | 4.4 |
| pH (1% solution) | 7.3 |
| Bulk Density g/cc | 0.56 |
| $CO_2$ evolution on dissolution ml/10 g | 27.3 |
| Oil Absorbency | 75 |
| Rate of solution (min) | 2.8 |
| Screen size −10/+100 | 85.8 |
| +10 | 0.2 |
| +40 | 43.4 |
| +100 | 89.0 |
| −100 | 11.0 |

EXAMPLE 5

In a P.K. blender were dry mixed 3840 g of STPP powder, 97.5 g sodium bicarbonate and 1702.5 g sodium carbonate and to this blend was added through an atomising dispersing bar 1860 g of polyphosphoric acid (81% $P_2O_5$). The resulting powder had a pH of 7.0 on solution.

2200 g of this powder was placed in a Hobart mixer and 120 ml of water were sprayed on the powder while mixing to produce a granular product which had the following characteristics:

| | |
|---|---|
| STPP added | 48.6% |
| $Na_2CO_3$ added | 21.5% |
| 81% $P_2O_5$ acid added | 23.5% |
| $NaHCO_3$ added | 1.2% |
| $H_2O$ added | 5.2% |
| pH (1% solution) | 7.0 |
| Bulk Density −10/+80 | 0.61 g/cc |
| % Oil Absorbency | 65 |
| Screen size −10 + 100 | 86.7% |
| +10 | 3.8% |
| 10/20 | 27.6% |
| 20/40 | 32.8% |
| 40/80 | 23.2% |
| 80/100 | 2.9% |
| −100 | 9.5% |

EXAMPLE 6

To 5000 g of STPP powder in a P.K. blender was added 1300 g of 81.9% $P_2O_5$ polyphosphoric acid to give a dry free-flowing powder. An additional 1666 g of STPP powder was added to the blender. Through an atomizing dispersing bar in the P.K. blender was added 285.6 g of sodium carbonate solution (33.3 wt. % $Na_2CO_3$) to the powdered blend while mixing. A granular product of the following characteristics was obtained:

| | |
|---|---|
| STPP added | 81.7% |
| $Na_2CO_3$ added | 2.0% |
| 81.9% $P_2O_5$ acid added | 12.5% |
| $H_2O$ added | 3.9% |
| pH (1% solution) | 6.9 |
| Bulk Density −10/+80 g/cc | 0.64 |
| % Oil Absorbency | 65 |
| Screen size −10 + 100 | 92.0 |
| +10 | 1.4 |
| 10/20 | 15.4 |
| 20/40 | 36.4 |
| 40/80 | 37.3 |
| 80/100 | 2.0 |
| −100 | 7.5 |

EXAMPLE 7

87 parts by weight of STPP powder was placed in a Marion Mixer and 11 parts by weight of 81.9% $P_2O_5$ acid sprayed on while mixing to give a dry free-flowing powder. 1000 g of the mixture was placed in a rotating drum and a solution of 20 g of sodium carbonate and 200 g $H_2O$ were atomized onto the surface of the rolling bed.

The mix granulated to give a product having the following characteristics:

| | |
|---|---|
| STPP added | 72.8% |
| $Na_2CO_3$ added | 2.0% |
| 81.9% $P_2O_5$ added | 9.2% |
| $H_2O$ added | 16.4% |
| Bulk Density −10/+80 g/cc | 0.58 |
| Screening | |
| +10 | 0.4 |
| 10/20 | 11.8 |
| 20/40 | 45.0 |
| 40/60 | 15.3 |
| 60/80 | 6.7 |
| 80/100 | 3.5 |
| −100 | 17.3 |
| Oil Absorbency | 75% |

EXAMPLE 8

5167.5 g of STPP powder was blended in a P.K blender with 84.5 g of $NaHCO_3$ and onto this mixture was sprayed through a dispersion bar, 78.0 g of 76.0% $P_2O_5$ polyacid to produce a dry powder. To the powder 455 g of $H_2O$ was added to give a product having the following characteristics:

| | |
|---|---|
| STPP added | 79.7% |
| $NaHCO_3$ added | 1.3% |
| 76.0% $P_2O_5$ acid added | 12.0% |
| $H_2O$ | 7.0 |
| Bulk Density (−10 + 80) g/cc | 0.76 |
| % Oil Absorbency | 50 |
| pH (1% solution) | 6.95 |
| Screen size | |
| +10 | 0.1 |
| 10/20 | 17.6 |
| 20/40 | 70.0 |
| 40/60 | 11.0 |
| 60/80 | 0.7 |
| 80/100 | 0.4 |
| −100 | 0.2 |

SUMMARY

The present invention, therefore, provides a low density, free-flowing, granular phosphate product having a high oil absorbency by using high $P_2O_5$ polyphosphoric acid. Modifications are possible within the scope of the invention.

I claim:

1. A dry, free-flowing, granular composition comprising granules formed from about 45 to about 85% by weight of a hydratable alkali metal phosphate selected from the group consisting of sodium tripolyphosphate, tetrasodium pyrophosphate, tetrapotassium pyrophosphate, tripotassium phosphate and dipotassium phosphate;

about 9 to about 30% by weight of polyphosphoric acid having a $P_2O_5$ content of about 75 to about 85%;

about 1.5 to about 23% by weight of sodium carbonate and/or sodium bicarbonate; and about 4 to about 17% by weight of water, said granules having a bulk density of about 0.5 to about 0.8 g/cc and an oil absorbency of about 50 to about 80%;

said alkali metal phosphate, said polyphosphoric acid and said sodium carbonate and/or sodium bicarbonate being present in amounts to provide an aqueous solution of pH of about 7 to about 8 upon dissolving the composition in water.

2. The composition of claim 1 comprising:

about 65 to about 75.5% by weight of said hydratable alkali metal phosphate, about 9.2 to about 30% by weight of said polyphosphoric acid, about 1.8 to about 23% by weight of said sodium carbonate and/or sodium bicarbonate, and about 4 to about 15% by weight of water.

3. The composition of claim 1 wherein said density is about 0.55 to about 0.65 g/cc.

4. The composition of claim 1 wherein said oil absorbency is about 65 to 75%.

5. The composition of claim 1 wherein said alkali metal phosphate is sodium tripolyphosphate.

6. The composition of claim 1 wherein said polyphosphoric acid has a $P_2O_5$ content of about 81 to 82%.

7. A method of forming a low density, dry, free-flowing, granular phosphate composition, which comprises:

forming a dry, free-flowing mixture of (1) a hydratable alkali metal phosphate selected from the group consisting of sodium tripolyphosphate, tetrasodium pyrophosphate, tetrapotassium pyrophosphate, tripotassium phosphate and dipotassium phosphate, (2) a polyphosphoric acid having a $P_2O_5$ content of about 75 to about 85%, and (3) sodium carbonate and/or sodium bicarbonate, the relative quantities of said alkali metal phosphate, polyphosphoric acid and sodium carbonate and/or sodium bicarbonate being such that the mixture, if dissolved in water, would result in a solution having a pH of about 7 to 8, and granulating said mixture with water to cause reaction between diluted polyphosphoric acid and part of said sodium carbonate and/or sodium bicarbonate to evolve carbon dioxide and form an expanded dry, free-flowing, granular phosphate composition having a bulk density of about 0.5 to about 0.8 g/cc and an oil absorbency in the range of about 50 to about 80%, the overall quantities of the components of the composition being:

about 45 to about 85% by weight of said hydratable alkali metal phosphate, about 9 to about 30% by weight of said polyphosphoric acid, about 1.5 to about 23% by weight of said sodium carbonate and/or sodium bicarbonate, and about 4 to about 17% by weight of water.

8. The method of claim 7 wherein said mixture of alkali metal phosphate, polyphosphoric acid, and sodium carbonate and/or sodium bicarbonate is formed by mixing together in a single step the components of said mixture.

9. The method of claim 7 wherein said mixture of alkali metal phosphate, polyphosphoric acid, and sodium carbonate and/or sodium bicarbonate is formed by first mixing the phosphate, polyphosphoric acid, and sodium carbonate and/or sodium bicarbonate to form a first mixture which would provide a solution of pH about 4 to 4.5 if dissolved in water, and subsequently mixing said first mixture with sodium carbonate and/or sodium bicarbonate and/or phosphate to form said mixture capable of providing an aqueous solution of pH about 7 when dissolved in water.

10. The method of claim 7, wherein the water is applied in the form of a fine mist during said granulation.

11. A method of forming a low density, dry, free-flowing, granular phosphate composition, which comprises:

forming a dry, free-flowing mixture of (1) a hydratable alkali metal phosphate selected from the group consisting of sodium tripolyphosphate, tetrapotassium pyrophosphate, tripotassium phosphate and dipotassium phosphate, and (2) a polyphosphoric acid having a $P_2O_5$ content of about 75 to about 85%, and granulating said mixture with an aqueous solution of sodium carbonate and/or sodium bicarbonate to cause reaction between diluted polyphosphoric acid and part of said sodium carbonate and/or sodium bicarbonate to evolve carbon dioxide and form an expanded dry, free-flowing, granular phosphate composition having a bulk density of about 0.5 to about 0.8 g/cc and an oil absorbency in the range of about 50 to about 80%, the overall quantities of the components of the composition being:

about 45 to about 85% by weight of said hydratable alkali metal phosphate, about 9 to about 30% by weight of said polyphosphoric acid, about 1.5 to about 23% by weight of said sodium carbonate and/or sodium bicarbonate, and about 4 to about 17% by weight of water, the relative quantities of said alkali metal phosphate, polyphosphoric acid and sodium carbonate and/or sodium bicarbonate being such that the product, if dissolved in water, would result in a solution having a pH of about 7 to 8.

12. The method of claim 11 wherein said mixture of alkali metal phosphate and polyphosphoric acid is formed by mixing together the components of the mixture in a single step.

13. The method of claim 11 wherein the aqueous sodium carbonate and/or sodium bicarbonate solution is applied in the form of a fine mist during said granulation.

* * * * *